US008691075B2

(12) United States Patent
Lica

(10) Patent No.: US 8,691,075 B2
(45) Date of Patent: Apr. 8, 2014

(54) METHOD FOR MEASURING ANALYTE CONCENTRATION IN A LIQUID SAMPLE

(75) Inventor: Georgeta Lica, Indianapolis, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 1001 days.

(21) Appl. No.: 12/649,929

(22) Filed: Dec. 30, 2009

(65) Prior Publication Data

US 2011/0155588 A1   Jun. 30, 2011

(51) Int. Cl.
*G01N 33/487* (2006.01)

(52) U.S. Cl.
USPC .......... 205/792; 204/403.01; 204/403.15; 205/777.5

(58) Field of Classification Search
USPC .......... 204/403.01–403.15; 205/777.5, 778, 205/792
See application file for complete search history.

(56) References Cited

U.S. PATENT DOCUMENTS

| | | | |
|---|---|---|---|
| 4,805,624 A | 2/1989 | Yao et al. | |
| 4,897,162 A | 1/1990 | Lewandowski et al. | |
| 5,873,990 A | 2/1999 | Wojciechowski et al. | |
| 5,980,708 A | 11/1999 | Champagne et al. | |
| 6,261,780 B1 | 7/2001 | Ogawa et al. | |
| 6,664,407 B2 | 12/2003 | James et al. | |
| 6,664,776 B2 | 12/2003 | Olofsson | |
| 7,045,054 B1 | 5/2006 | Buck et al. | |
| 2002/0164671 A1 | 11/2002 | James et al. | |
| 2003/0094383 A1* | 5/2003 | Kermani | 205/777.5 |
| 2003/0113933 A1 | 6/2003 | Jansson et al. | |
| 2004/0094432 A1* | 5/2004 | Neel et al. | 205/777.5 |
| 2006/0096870 A1 | 5/2006 | Sheu et al. | |
| 2007/0235346 A1 | 10/2007 | Popovich et al. | |
| 2008/0000780 A1* | 1/2008 | Tonks | 205/792 |
| 2008/0156662 A1 | 7/2008 | Wu et al. | |
| 2008/0173552 A1 | 7/2008 | Wu et al. | |
| 2008/0179197 A1 | 7/2008 | Wu | |

FOREIGN PATENT DOCUMENTS

| | | |
|---|---|---|
| EP | 0 637 808 A2 | 2/1995 |
| EP | 0 987 544 A1 | 3/2000 |
| EP | 1 707 636 A1 | 10/2006 |
| WO | WO 2004/053476 A1 | 6/2004 |
| WO | WO 2005/001463 A1 | 1/2005 |
| WO | WO 2006/042304 A1 | 4/2006 |
| WO | WO 2007/013915 A1 | 2/2007 |

OTHER PUBLICATIONS

International Patent Application PCT/EP2010/007930 International Preliminary Report on Patentability mailed Apr. 13, 2012.

(Continued)

*Primary Examiner* — Bach Dinh
(74) *Attorney, Agent, or Firm* — Woodard, Emhardt, Moriarty, McNett & Henry LLP

(57) ABSTRACT

The blood glucose analysis technique and system described herein address the issue of hematocrit interference when rapidly detecting glucose concentrations. It addresses this issue by using a differential pulse voltammetry technique in which short high, frequency voltage pulses are applied to keep the diffusion layer within the reagent of the working electrode, and the pulses are applied in a limited voltage window (or range) that is below the peak, diffusion-limited current. The readings below the peak are then used to determine glucose concentrations. With this technique, glucose concentrations can be determined relatively fast (e.g., within 5 seconds) and independently of the hematocrit levels of the fluid being analyzed.

25 Claims, 18 Drawing Sheets

(56) References Cited

OTHER PUBLICATIONS

Differential pulse voltammetry—Wikipedia, the free encyclopedia. [retrieved Aug. 29, 2008]. Retrieved from the Internet: <URL: http://en.wikipedia.org/wiki/ Differential_pulse_voltammetry>.
Electrochemistry Software Electrochemist.com 5.8—Dr. Huang. [retrieved Jul. 18, 2008]. Retrieved from the Internet: <URL: http://www.drhuang.com/science/chemistry/electrochemistry/polar.doc.htm>.
Hari Gunasingham et al., "Pulsed amperometric detection of glucose using a mediated enzyme electrode", Journal of Electroanalytical Chemistry 287, 349-362 (1990).
Larissa I. Netchiporouk et al., In Vivo Brain Glucose Measurements: Differential Normal Pulse Voltammetry with Enzyme-Modified Carbon Fiber Microelectrodes, Anal. Chem., Dec. 15, 1996, 4358-4364.
M. Lambrechts et al., "Biosensors: Microelectrochemical Devices", 85-88 (1992).
Improved-Accuracy Biosensor Strip for Accu-Chek Advantage, Presented Orally at ACS Boston Meeting, Burke, David W. and Surridge, Nigel A., ~1993-1994.
International Patent Application No. PCT/EP2010/007930 Search Report mailed May 16, 2011.
International Patent Application No. PCT/EP2010/007930 International Search Report and Written Opinion mailed Jun. 22, 2011.

* cited by examiner

METHOD FOR MEASURING ANALYTE CONCENTRATION IN A LIQUID SAMPLE

BACKGROUND

Recently, there has been a trend for patients to self monitor various health conditions. For example, diabetics traditionally monitor blood glucose levels a number of times a day. Due to its nature, glucose monitoring requires a high level of accuracy of the reported glucose values with little to no interference by other substances contained in the sample. Other types of body fluid tests require similar features.

The most common techniques for measuring glucose levels in blood or interstitial fluid utilize electrochemical techniques. Electrochemical detection of glucose is typically based on the measurement of an electrical signal or property that is proportional to the analyte concentration. The signal is generated upon a direct or indirect redox reaction on or in the direct vicinity of the electrode surface. Some traditional electrochemical techniques include amperometry, coulometry, and/or impedance measurements. However, there are several drawbacks with respect to these techniques. Due to the diffusion-controlled nature of the measured signal, amperometric measuring techniques typically need a long measuring time and can be prone to interference from varying hematocrit levels. Although utilizing impedance measurement techniques can address these issues, impedance techniques typically require complicated and expensive equipment. For home diagnostic testing settings as well as in other medical areas, equipment cost is always a concern.

Thus, there is a need for improvement in this field.

SUMMARY

One aspect concerns a method for determining glucose concentration in a body fluid. The body fluid in a biosensor is analyzed through differential pulse voltammetry, and the biosensor at least includes a reagent covering a working electrode. The meter applies short, high frequency voltage pulses to the body fluid in the biosensor to keep the diffusion layer within the reagent of the working electrode, and the voltage of the pulses are incrementally increased. The meter determines the glucose concentration of the body fluid based on the response to the pulses within a voltage window that is below the peak, diffusion-limited current, and the meter outputs the glucose concentration results.

Another aspect concerns a method in which glucose concentration in a body fluid is analyzed through differential pulse voltammetry. One or more pulses are applied to the body fluid in a voltage window that is below the peak, diffusion-limited current. The glucose concentration is determined based on the response to the pulses in the voltage window.

A further aspect concerns a method in which analyte concentrations in a body fluid are analyzed by applying one or more voltage pulses in a limited voltage window that is below the peak, diffusion-limited current to the body fluid. The voltage pulses are short to keep the diffusion layer within the reagent of the working electrode. The glucose concentration is determined based on the response to the pulses in the limited voltage window.

Further forms, objects, features, aspects, benefits, advantages, and embodiments of the present invention will become apparent from a detailed description and drawings provided herewith.

DESCRIPTION OF SELECTED EMBODIMENTS

Figure 1:
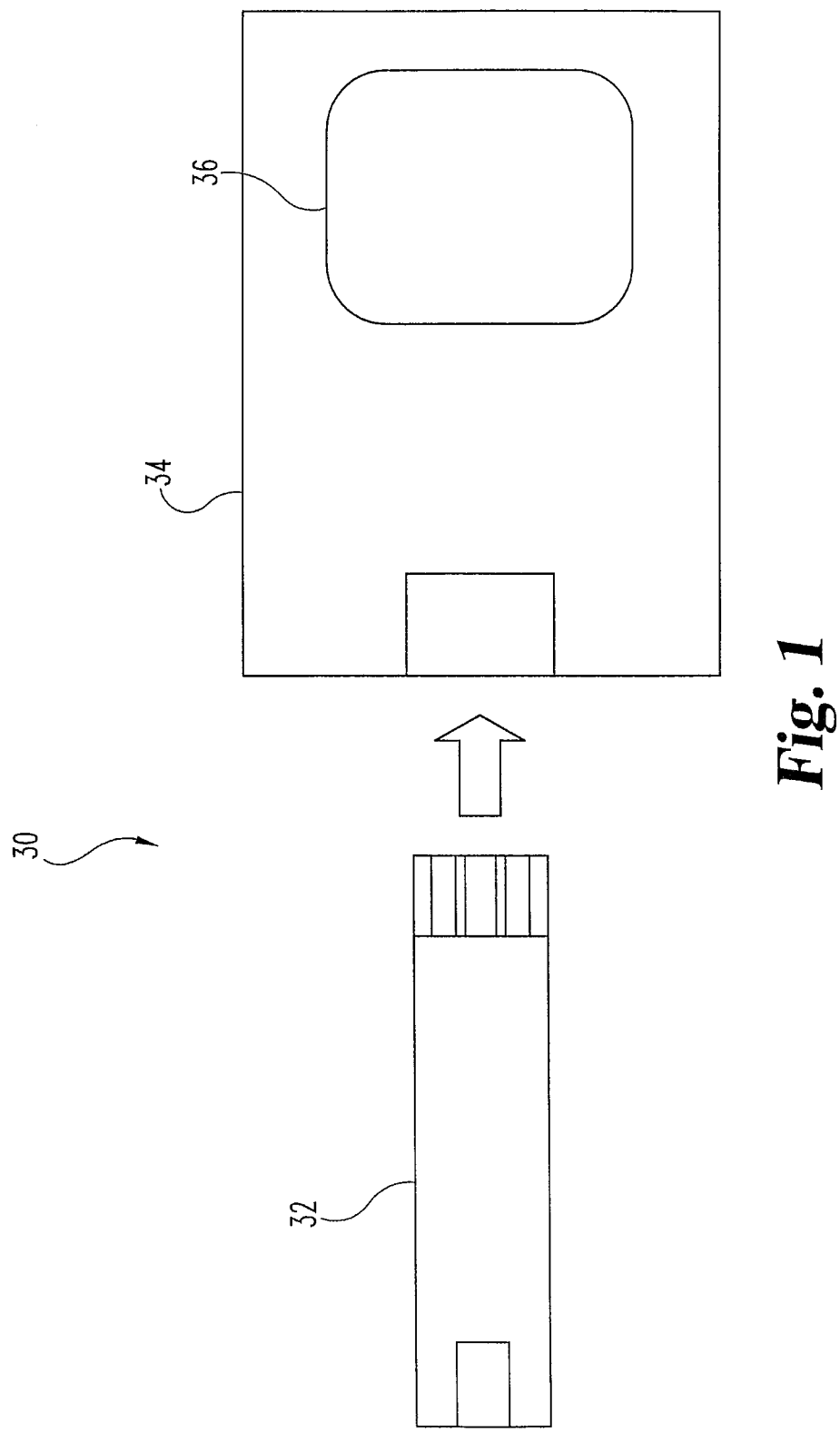
FIG. 1 is a diagrammatic view of a blood glucose monitoring system according to one embodiment that can use the differential pulse voltammetry technique described herein.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The body fluid analysis technique and system described herein address the issue of hematocrit interference when rapidly detecting analyte concentrations. It addresses this issue by using a pulsed voltammetry technique in which short, high frequency voltage pulses are applied to keep the diffusion layer within the reagent of the working electrode, and the pulses are sequentially increased within a limited voltage window (or range) that is below the voltage which creates the peak, diffusion-limited current. The readings below the peak, diffusion-limited current are then used to determine glucose concentrations. With this technique, glucose concentrations can be determined relatively fast (e.g., within 5 seconds) and generally independent of the hematocrit levels of the fluid being analyzed. While not certain, it is theorized the relatively short pulses ensure that the diffusion layer remains in the reagent layer so that the observed current is generated by the analyte diffused inside the reagent layer. Consequently, there is less interference from the red blood cells.

The technique can be used to analyze glucose concentrations using two-electrode or three-electrode (or more) electrochemical type test strips. Depending on the electrode arrangement, the potential windows may vary. By using only direct current (DC) excitation at low potentials, the electronics and other systems in the meter can be simplified, and short measurement times can be achieved. For example, the test can be completed within 5 seconds (or less) of drop detection. Moreover, the low applied potential can eliminate the contribution of common interferants to the current response, thereby providing more accurate results.

An example of a glucose monitoring system 30 that is configured to measure analyte levels using the Differential Pulse Voltammetry (DPV) technique as described herein is illustrated in FIG. 1. The system 30 includes a biosensor 32, which in the illustrated example is a test strip, and a meter 34. As depicted, the test strip 32 is attached to the meter 34, and the results from the analysis are provided on output device 36. Biosensors and meters are commonly known in the art, and for the sake of brevity, they will not be discussed at great detail below. As mentioned before, there has been some difficulty in rapidly and inexpensively analyzing fluid samples using traditional electrochemical analysis techniques in which the blood samples used have varying degrees of hematocrit. The inventors have discovered a unique technique and system for addressing the issue of hematocrit interference when rapidly detecting analyte concentrations. In particular, a DPV technique is used in which short, high-frequency voltage pulses are applied in a limited voltage window or range that is below the peak, diffusion-limited current. The resulting response signal is then used to determine analyte concentrations such as glucose levels. Using this technique, glucose concentrations can be determined relatively fast with little hematocrit interference, and the electronic components within the meter 34 can be relatively inexpensive.

Figure 2:
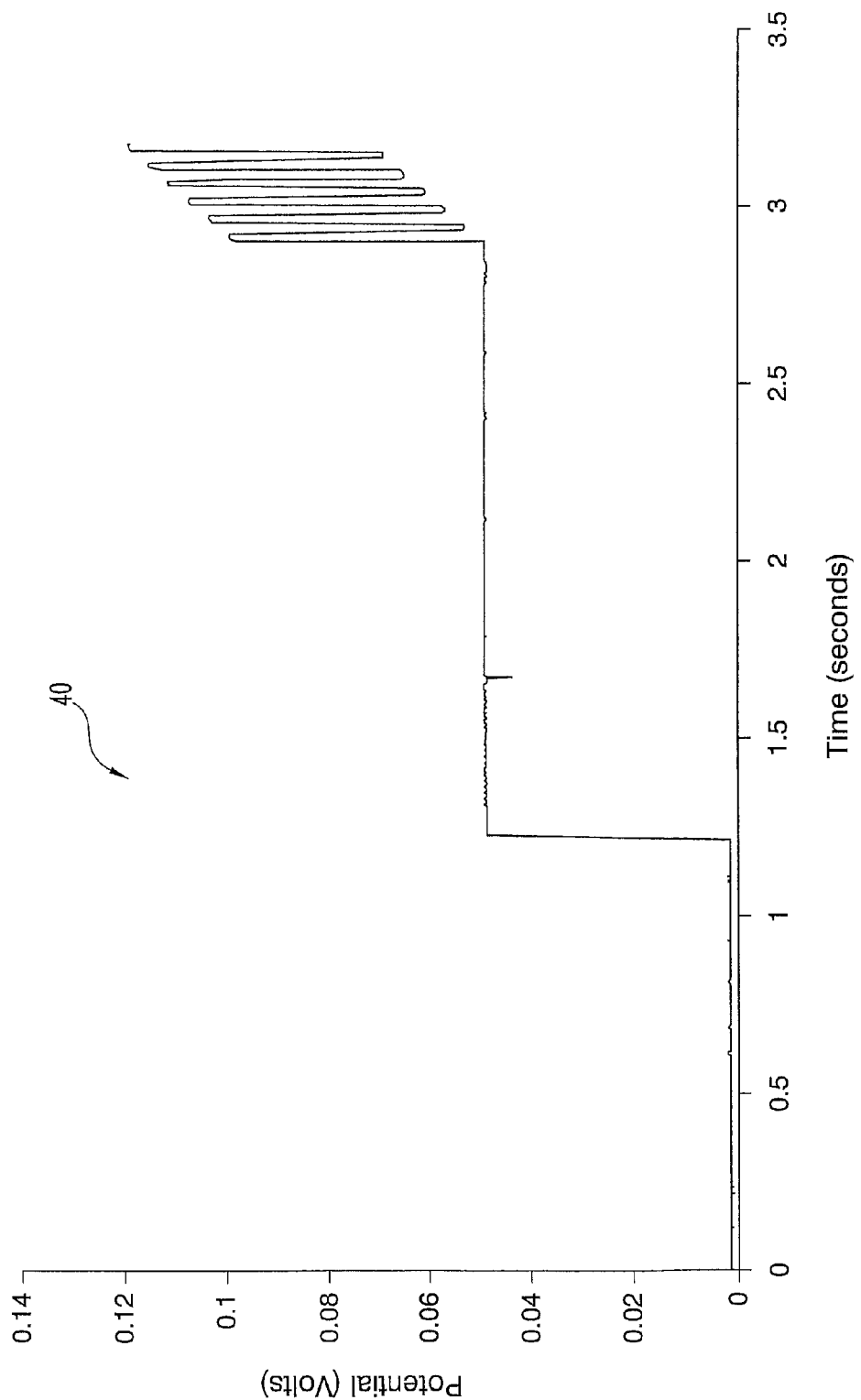
FIG. 2 illustrates an example of a voltage signal that can be applied to a body fluid sample in accordance with the differential pulse voltammetry technique described.

FIG. 2 is a graph 40 that illustrates an example of an applied potential waveform used to analyze a fluid sample with, for example, the glucose monitoring system 30 of FIG. 1. The graph 40 illustrates the potential waveform applied by the meter 34 to the test strip 32 during analysis. In one example, a solution containing glucose, such as blood, is applied to a test strip 32, and after the solution diffuses through the capillary in the electrochemical zone containing the electrodes and reagent, a potential waveform, like the one illustrated in FIG. 1, is applied. As can be seen in FIG. 1, when the bodily fluid is initially applied to the test strip 32, there is a quiet time or incubation period that allows sufficient time for enzymatic reaction to occur. In the illustrated example, the incubation period is around 3 seconds, but in other examples, the incubation period can be longer or shorter. For instance, it can include a 2 second incubation period or no incubation period at all.

After the incubation period, the meter 34 applies a series of pulses at ever increasing potentials. In one example, 50 millivolt (mV) pulses are applied for 25 milliseconds (msec) and are repeated every 25 msec. For every pulse, the baseline pulse increases in this example by 4 mV increments. In one particular example, the pulses are in the form of symmetrical waves that are superimposed on a staircase-shaped waveform in which the period of the symmetrical wave is identical to the time step of the staircase wave.

Figure 3:
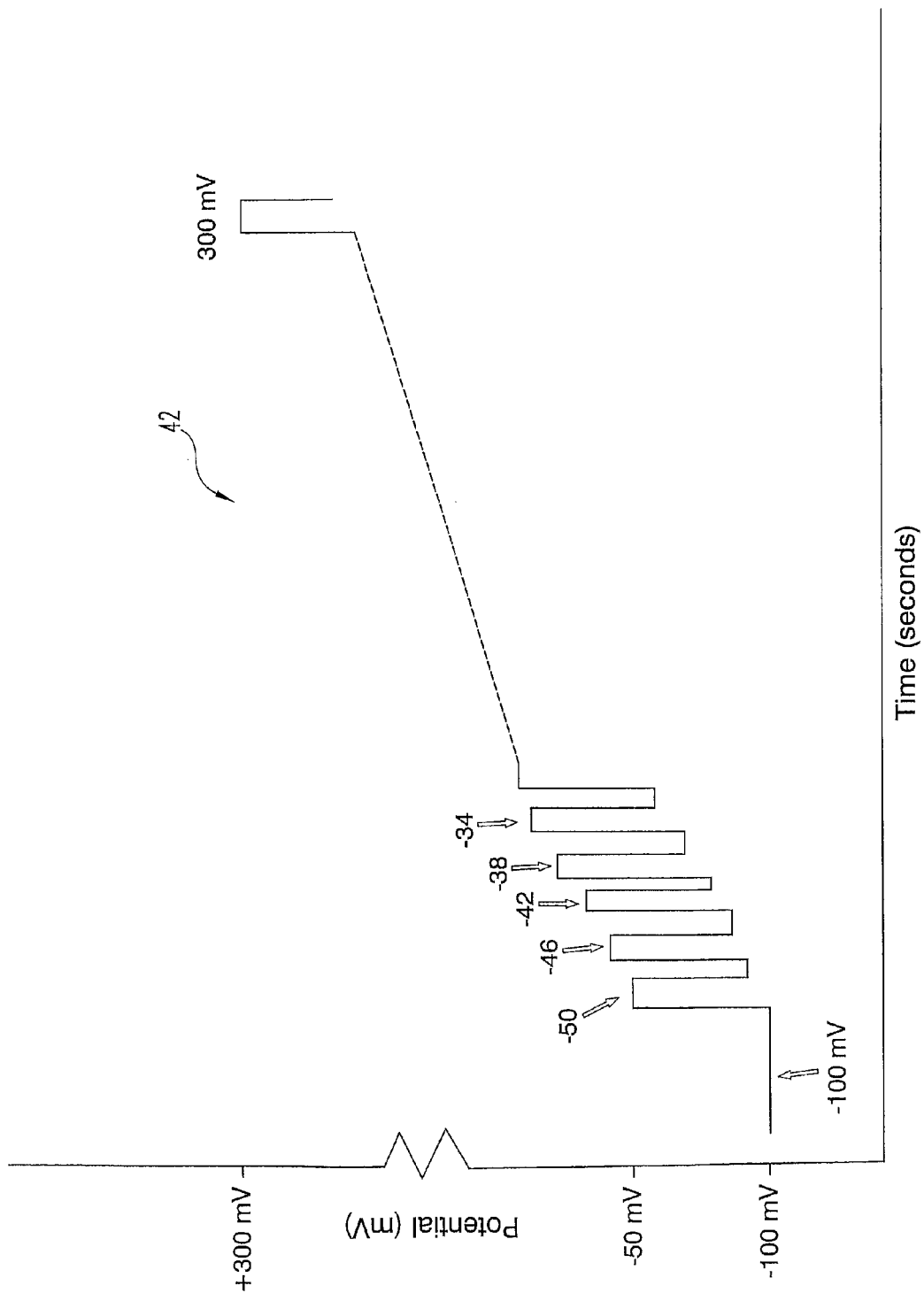
FIG. 3 shows an example of another differential pulse voltammetry waveform showing the evolution of the signal over time.

Other type of wave forms can be used for analyzing the body fluid. For instance, FIG. 3 illustrates an example of a waveform in which 50 mV pulses are applied and increase by 4 mV increments within a potential window of −100 mV to 300 mV.

Figure 4:
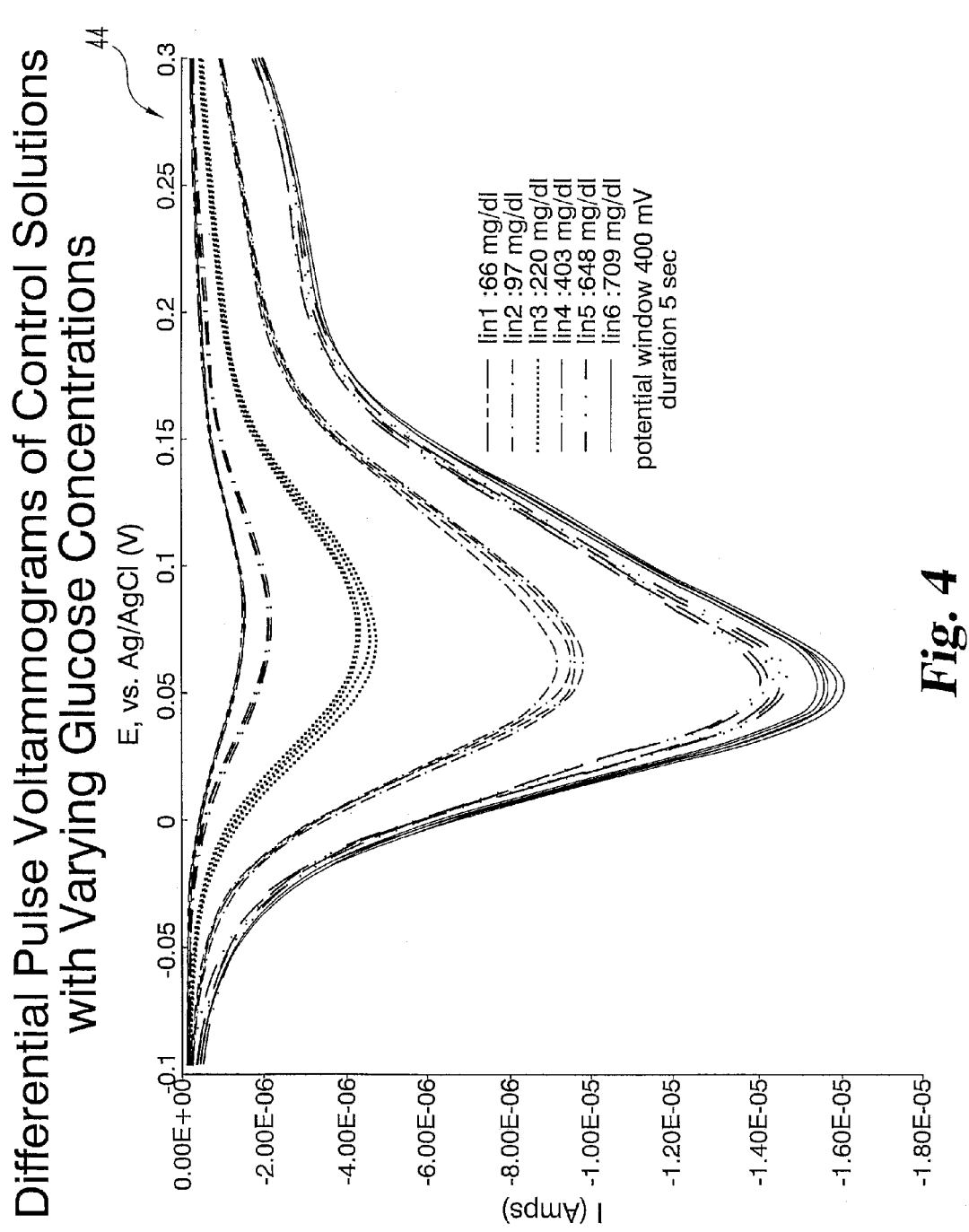
FIG. 4 is a differential pulse voltammogram of a control solution containing 66, 97, 220, 403, 648, and 709 mg/dl of glucose in which the potentials are reported in comparison to an Ag/AgCl reference electrode.
Figure 5A:
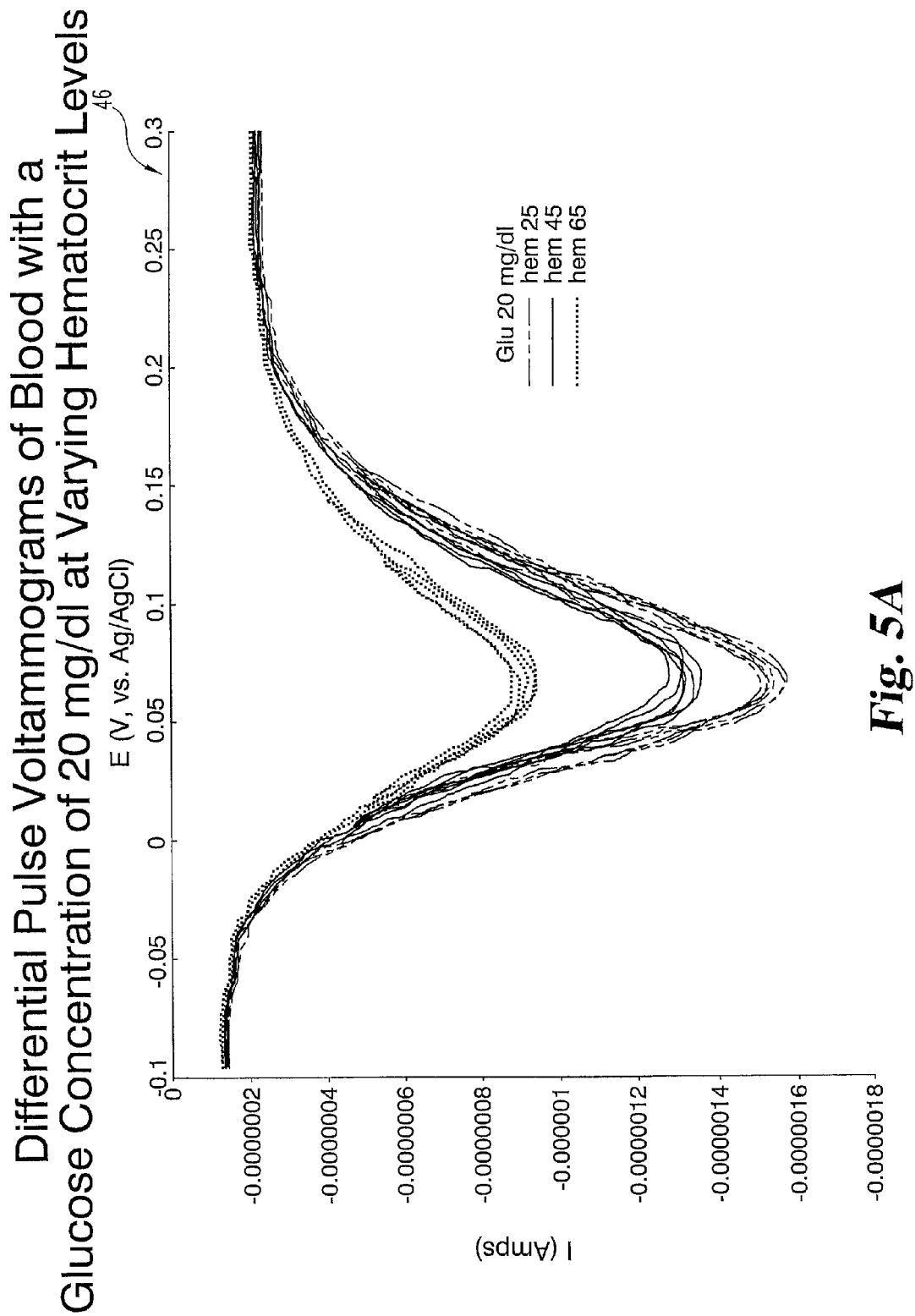
FIG. 5A is a differential pulse voltammogram of blood containing a target glucose concentration of 20 mg/dl and hematocrit levels of 25, 45, and 65 percent in which the potentials are in comparison to an Ag/AgCl reference electrode.
Figure 5B:
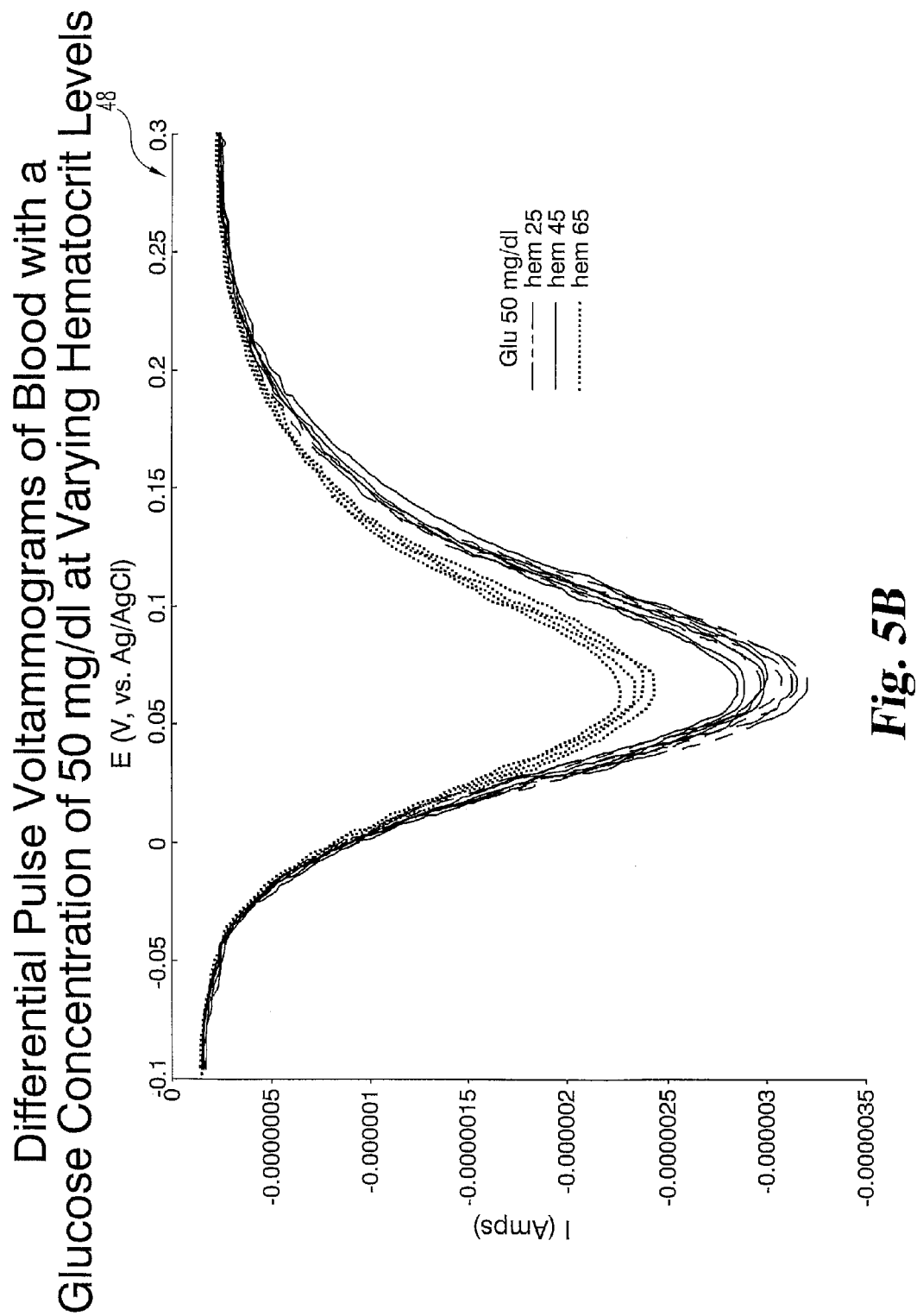
FIG. 5B is a differential pulse voltammogram of blood containing a target glucose concentration of 50 mg/dl and hematocrit levels of 25, 45, and 65 percent in which the potentials are in comparison to an Ag/AgCl reference electrode.
Figure 5C:
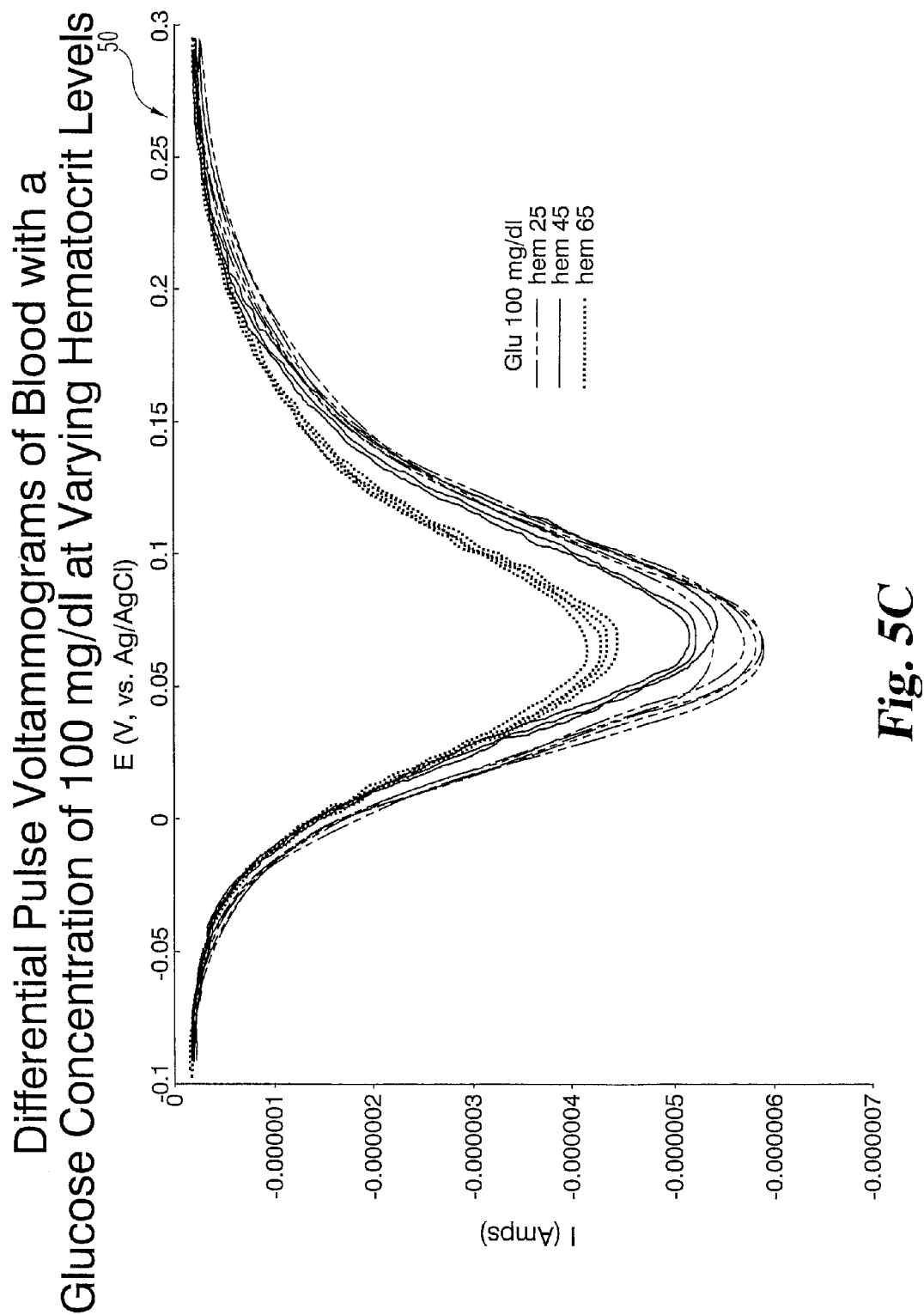
FIG. 5C is a differential pulse voltammogram of blood containing a target glucose concentration of 100 mg/dl and hematocrit levels of 25, 45, and 65 percent in which the potentials are in comparison to an Ag/AgCl reference electrode.
Figure 5D:
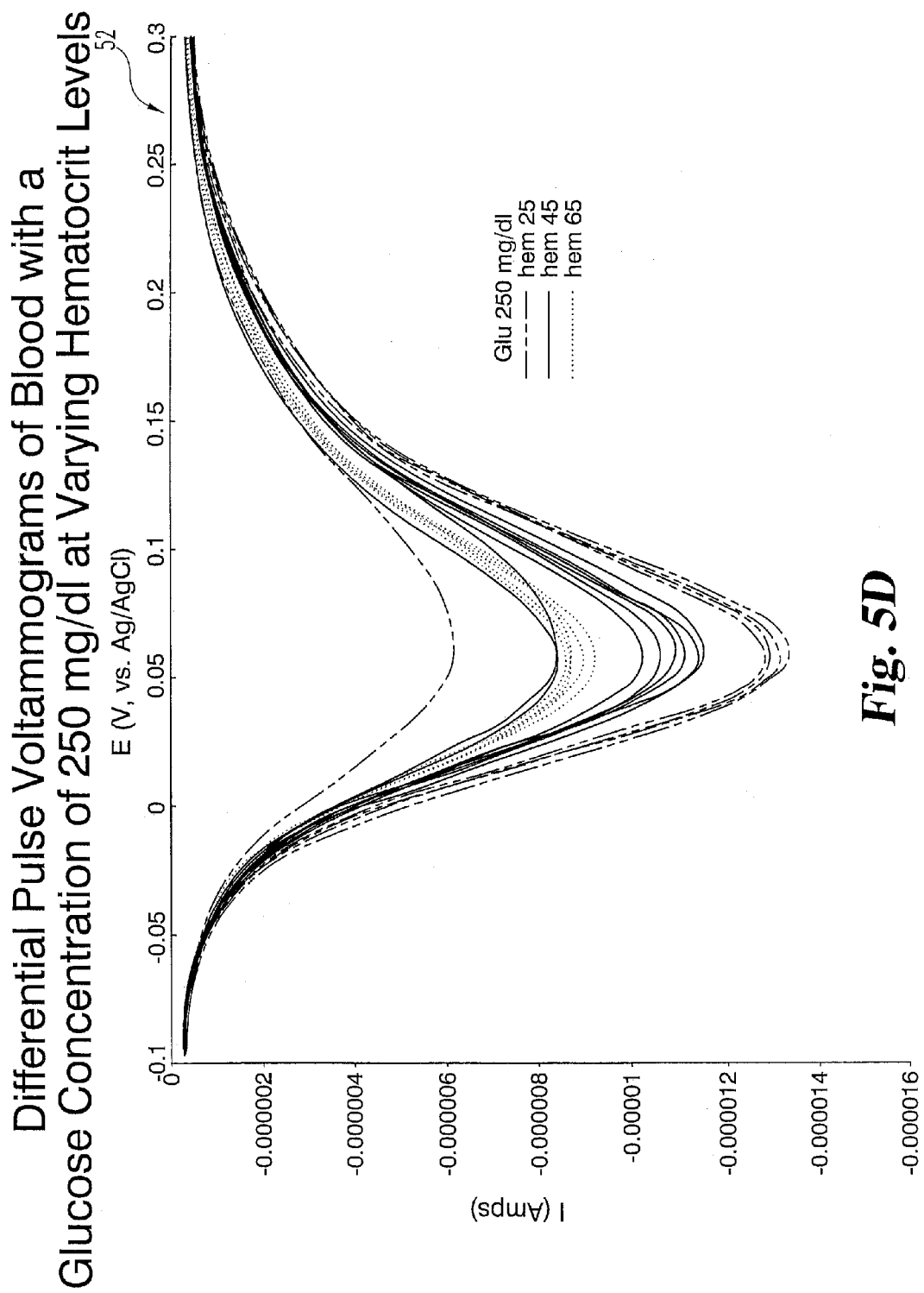
FIG. 5D is a differential pulse voltammogram of blood containing a target glucose concentration of 250 mg/dl and hematocrit levels of 25, 45, and 65 percent in which the potentials are in comparison to an Ag/AgCl reference electrode.
Figure 5E:
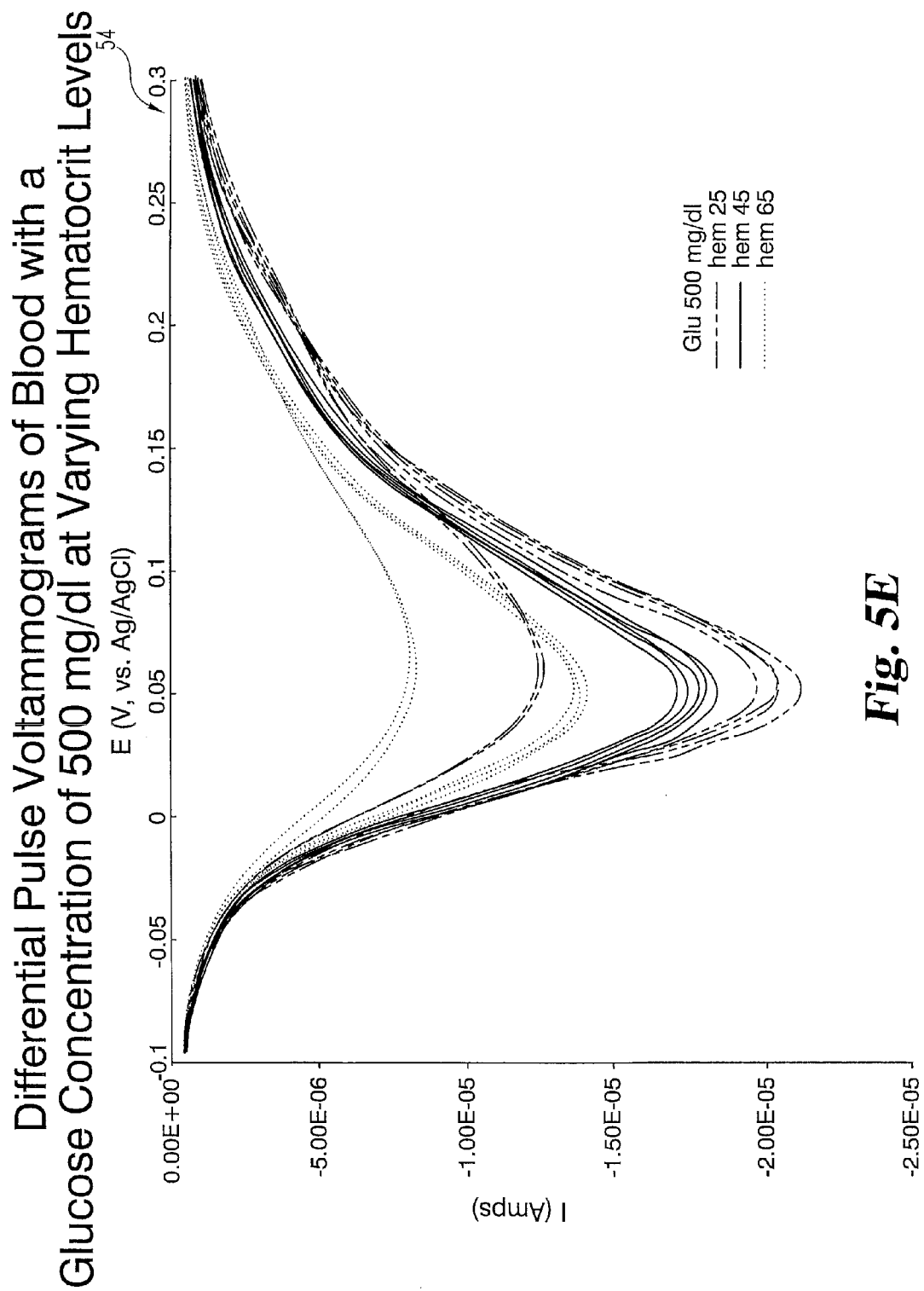
FIG. 5E is a differential pulse voltammogram of blood containing a target glucose concentration of 500 mg/dl and hematocrit levels of 25, 45, and 65 percent in which the potentials are in comparison to an Ag/AgCl reference electrode.

During analysis, the meter 34 measures the system response as the difference between the current at the end of the pulse and the current just before the pulse is applied. In other words, the signal current is the difference between the current sampled at the end of the positive pulse. FIG. 4 is a graph 44 that illustrates differential pulse voltammograms of control solutions with various glucose concentrations using this technique. Specifically, the graph 44 in FIG. 4 illustrates voltammograms for control solutions containing glucose concentrations of 66, 97, 220, 403, 648, and 709 mg/dl. The potential window was 400 mV, and the duration of the test lasted 5 seconds. For one example reagent chemistry, the glucose in the blood is converted to gluconolactone, and at the same time, the electrons generated by this reaction participate in the reduction of the mediator. By applying an increasingly positive potential, the oxidation of the reduced form of the mediator is induced. By pulsing the potential to more positive values, the current increase is proportional to the amount of reduced mediator converted respectively to glucose in the sample. The current peaks at a potential close to the standard redox potential of the oxidized/reduced couple of the mediator followed by a decrease in current when the rate of diffusion of the electroactive species to the electrode is lower than the redox reaction rate. This diffusion-limiting effect can be seen in the peaking of the curves shown in FIG. 4 in which the relative heights of the peaks generally increase with increasing glucose concentrations.

As mentioned before, variations in hematocrit levels can adversely affect glucose concentration readings, and therefore, there is a need to reduce the effect of hematocrit. To understand this issue, blood samples with hematocrit content adjusted to 25 percent, 45 percent, and 65 percent having various glucose concentrations of 25, 50, 100, 250, and 500 mg/dl were analyzed. FIGS. 5A, 5B, 5C, 5D, and 5E contain graphs 46, 48, 50, 52, and 54 that respectively illustrate differential pulse voltammograms for the blood sample with hematocrit concentrations at 25 percent, 45 percent, and 65 percent at glucose concentrations of 20, 50, 100, 250, and 500 mg/dl, respectively. In all of the graphs, the maximum peak, diffusion-limited current is at approximately 70 mV. By comparing the samples containing the same amount of glucose with different hematocrit levels, it can be observed that the peak current decreases when the hematocrit percentage increases. This illustrates the hematocrit effect in which the measured glucose concentrations deviate from the real glucose concentrations in samples having blood cell (hematocrit) content. Surprisingly, it was discovered that in the potential ranges that are below the peak, diffusion-limited current, the effect of hematocrit can be minimized. In particular, as can be seen in the graphs, in the potential window of −100 mV to 0 mV the hematocrit effect is negligible. Even in the potential range of −100 mV to 10 mV hematocrit effect is minimal. Thus, it was discovered that measuring readings below the peak, diffusion-limited current using a pulsed voltammetry technique in which short, high frequency voltage pulses are used helped to improve glucose concentration readings at varying hematocrit levels.

Figure 6A:
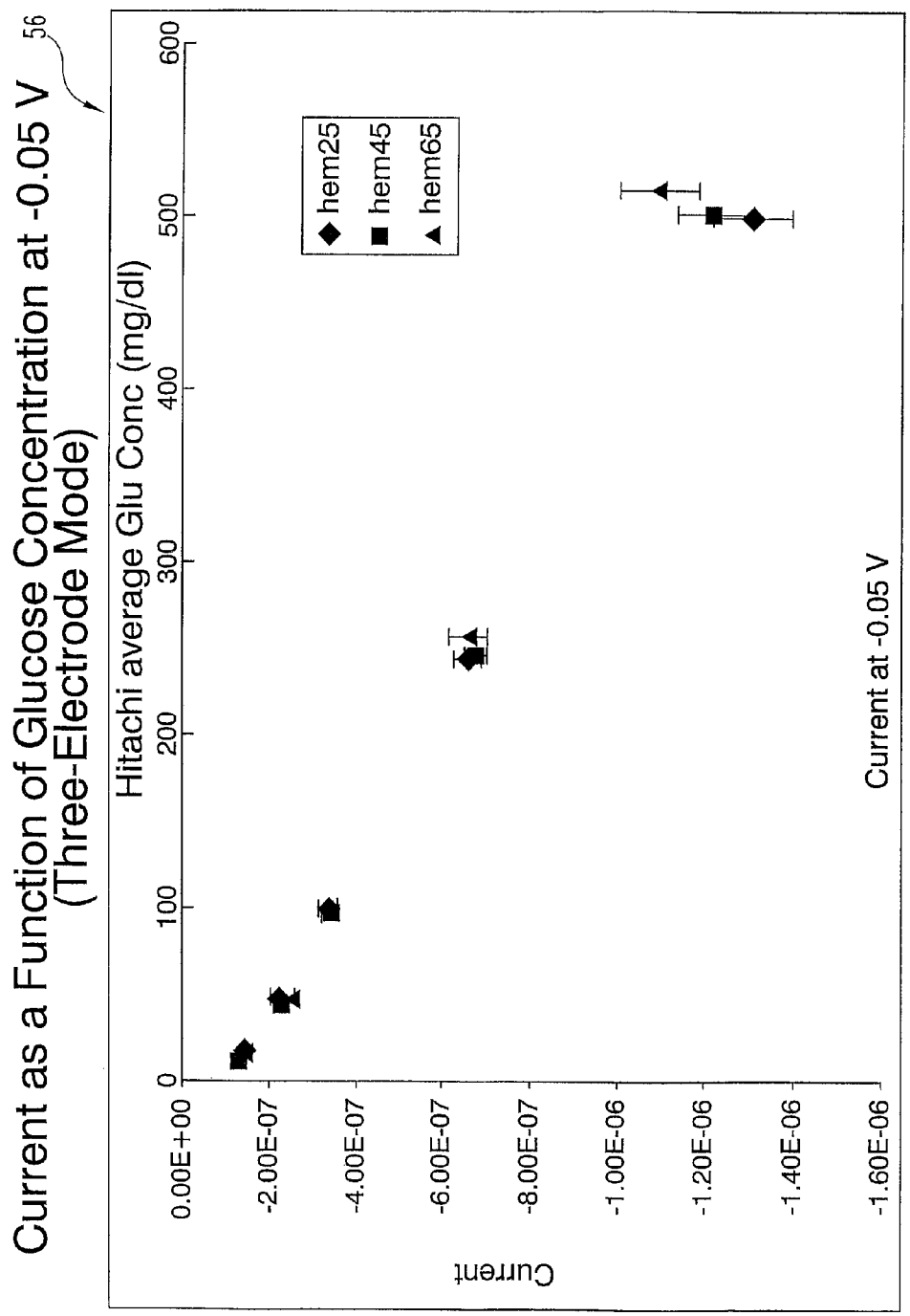
FIG. 6A is a graph illustrating current as a function of glucose concentration at −0.05 V with an average of 10 measurements performed with the same solution in a three-electrode mode.
Figure 6B:
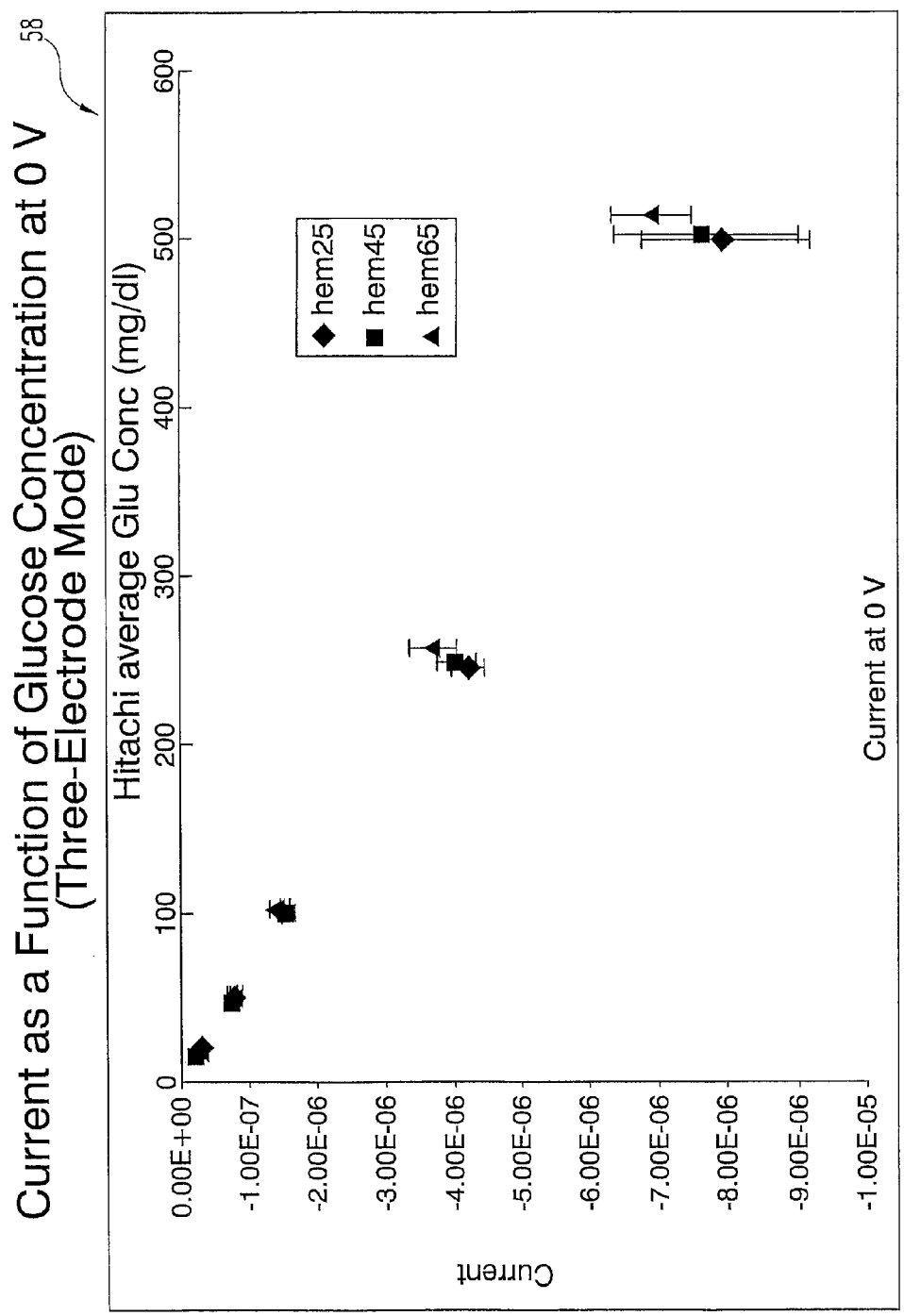
FIG. 6B is a graph illustrating current as a function of glucose concentration at 0.0 V with an average of 10 measurements performed with the same solution in a three-electrode mode.

To further reflect this improvement, FIG. 6A illustrates a graph 56 showing current as a function of glucose concentration at −0.05 mV, and FIG. 6B illustrates a graph 58 showing the current as a function of glucose concentration at 0 mV at 25 percent, 45 percent, and 65 percent hematocrit levels. As should be appreciated, the measurements in both of these graphs 56, 58 were taken using the above-described pulsed voltammetry technique in which the currents were measured below the diffusion-limited peak current (i.e., within the above-described potential windows). The testing was taken with respect to the above-described system in which the test strip 32 had three electrodes (i.e., working, counter, and reference electrodes). In particular, the potentials were measured with respect to the Ag/Ag Cl reference electrode. In FIGS. 6A and 6B, the arrow bars represent ±1 standard deviation. The current values were averaged over ten measurements performed with the same solution in which the hematocrit levels varied between 25 percent, 45 percent, and 65 percent. As can be seen, there is significant overlap in the average reading at all of the illustrated hematocrit levels as well as glucose concentrations.

As mentioned above, it is theorized that the relatively short, high frequency voltage pulses help to keep the diffusion layer within the reagent, thereby reducing the hematocrit effect. Using the previous 50 and 0 mV examples, the applied potential corresponds to a measurement time of 0.625 and 1.25 seconds, respectively, excluding the incubation period. Assuming radial diffusion, the diffusion layer thickness (d) at 0.625 seconds can be calculated according to Equation 1 below:

$$d = \sqrt{2Dt} \quad \text{EQUATION 1}$$

where:
d=diffusion layer thickness
D=diffusion coefficient
t=time

A diffusion coefficient (D) of $5*10^{-6}$ cm$^2$/sec is the characteristic of most analytes in an aqueous solution. Using Equation 1, the diffusion layer thickness (d) at 0.625 sec. (t) is 25 micrometers (μm). As mentioned before, the pulses are applied at 25 msec pulses. By applying a 25 msec pulse according to Equation 1, only 5 micrometers of the diffusion layer will be sampled. Consequently, the response current generated by the analyte is diffused into the reagent layer where red blood cells are less likely to be present. By having the measurements based on a voltage window that is below the redox potential of the oxidized/reduced couple (i.e., operating with no over potential), the kinetics of the reaction will become the limiting factor which in turn minimizes contribution from diffusion. As can be seen by these results, this technique is capable of accurately predicting glucose in a 20 to 500 mg/dl concentration range within minimum contribution from hematocrit as well as able to detect glucose in a rapid manner.

Figure 7A:
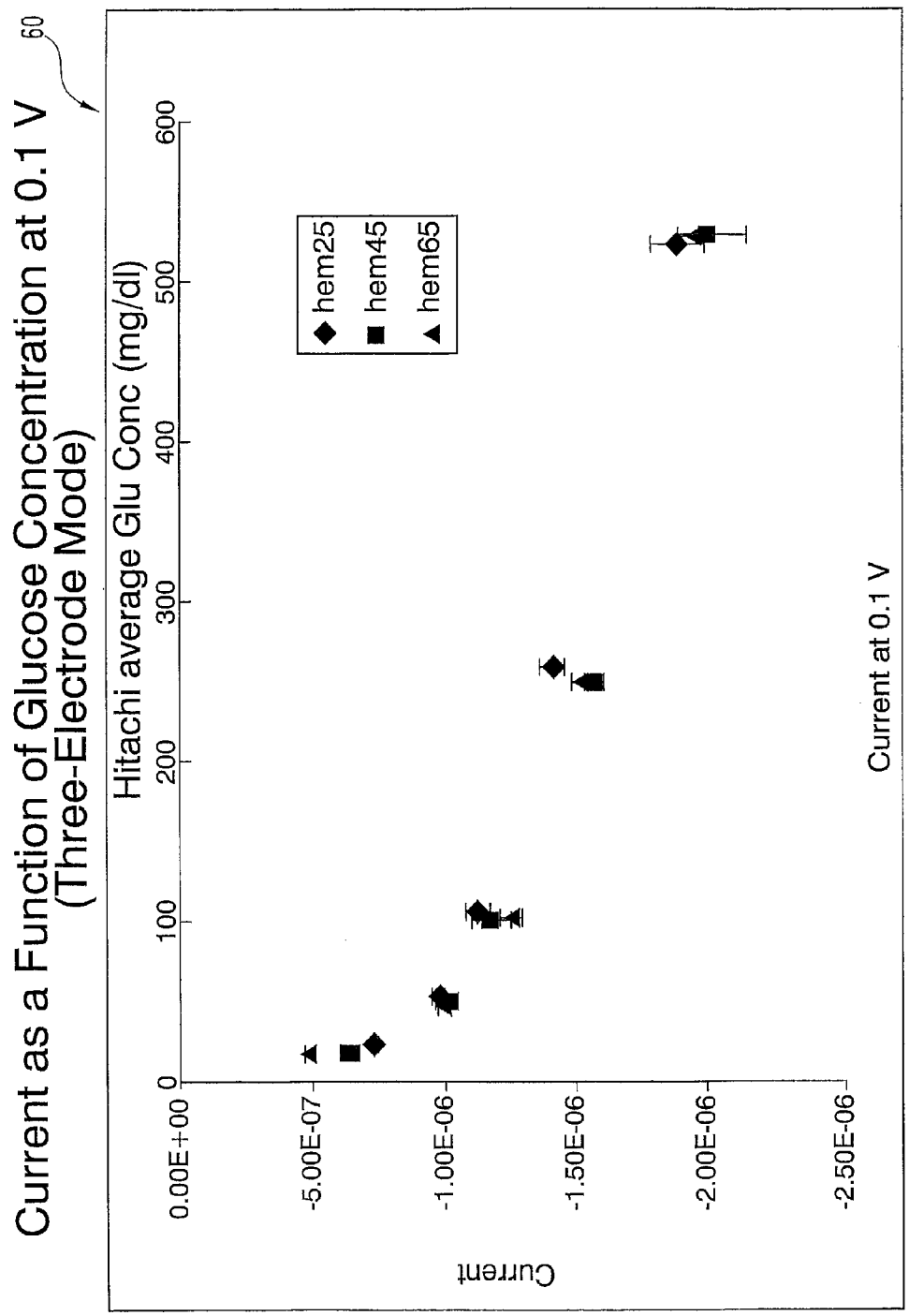
FIG. 7A is a graph illustrating current as a function of glucose concentration at 0.1 V with an average of 10 measurements performed with the same solution in a two-electrode mode.
Figure 7B:
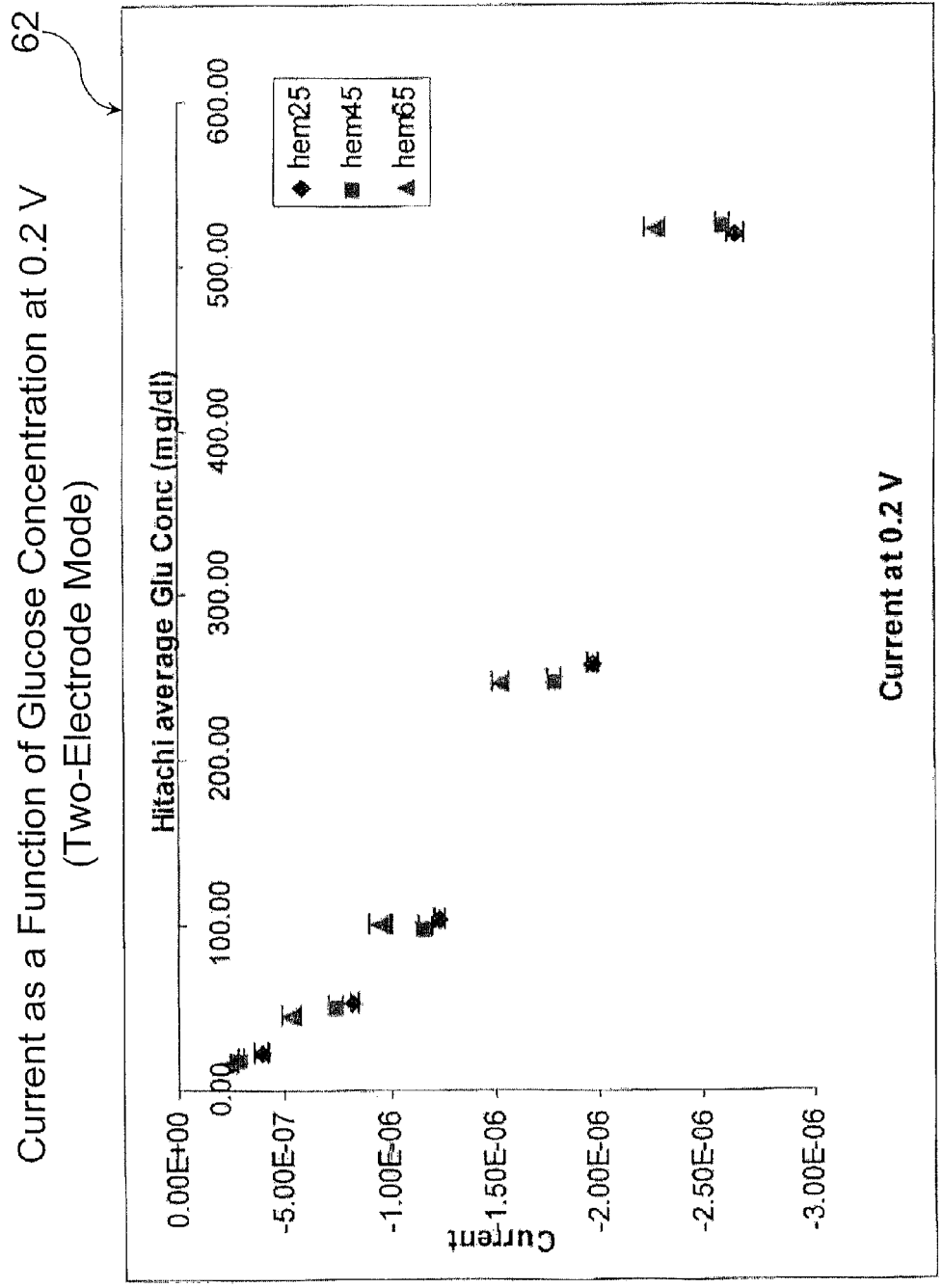
FIG. 7B is a graph illustrating current as a function of glucose concentration at 0.2 V with an average of 10 measurements performed with the same solution in a two-electrode mode.

In the previous examples, the test strip 32 was a three-electrode configuration, that is, a working, counter, and reference electrode mode in which an external Ag/AgCl reference electrode was used. It should be recognized that this technique can be adapted for use using only two electrodes. For example, the test strip 32 can include an Aviva® brand test strip manufactured by Roche Diagnostics. When the two-electrode strips 32 are used, the parameters were adjusted by changing the potential window to 0.5-0.55 volts. FIG. 7A contains a graph 60 showing current as a function of glucose concentration at 0.1 volts at 25 percent, 45 percent, and 65 percent hematocrit levels. FIG. 7B shows a graph 62 illustrating the resulting current as a function of glucose concentration at 0.2 volts using the two-electrode mode with hematocrit levels of 25, 45, and 65 percent. For both FIGS. 7A and 7B, the pulse lengths and pulse intervals were the same as above as well as the pulse voltages and voltage step. That is, the pulse length and pulse interval were 25 msec and the pulse voltage was 50 mV with a 4 mV step. The potential window ran from 0.5 to 0.55 volts. Although the responses shown in FIGS. 7A and 7B for the two-electrode mode appear to be less stable than the three-electrode mode, the graphs still show good sensitivity to glucose concentrations. Like the previous examples, the hematocrit effect is reduced by measuring the response at low potentials within the first few seconds of its measurement. In other words, the hematocrit effect is reduced by applying and measuring the pulses that are below the peak, diffusion-limited current level.

Figure 8A:
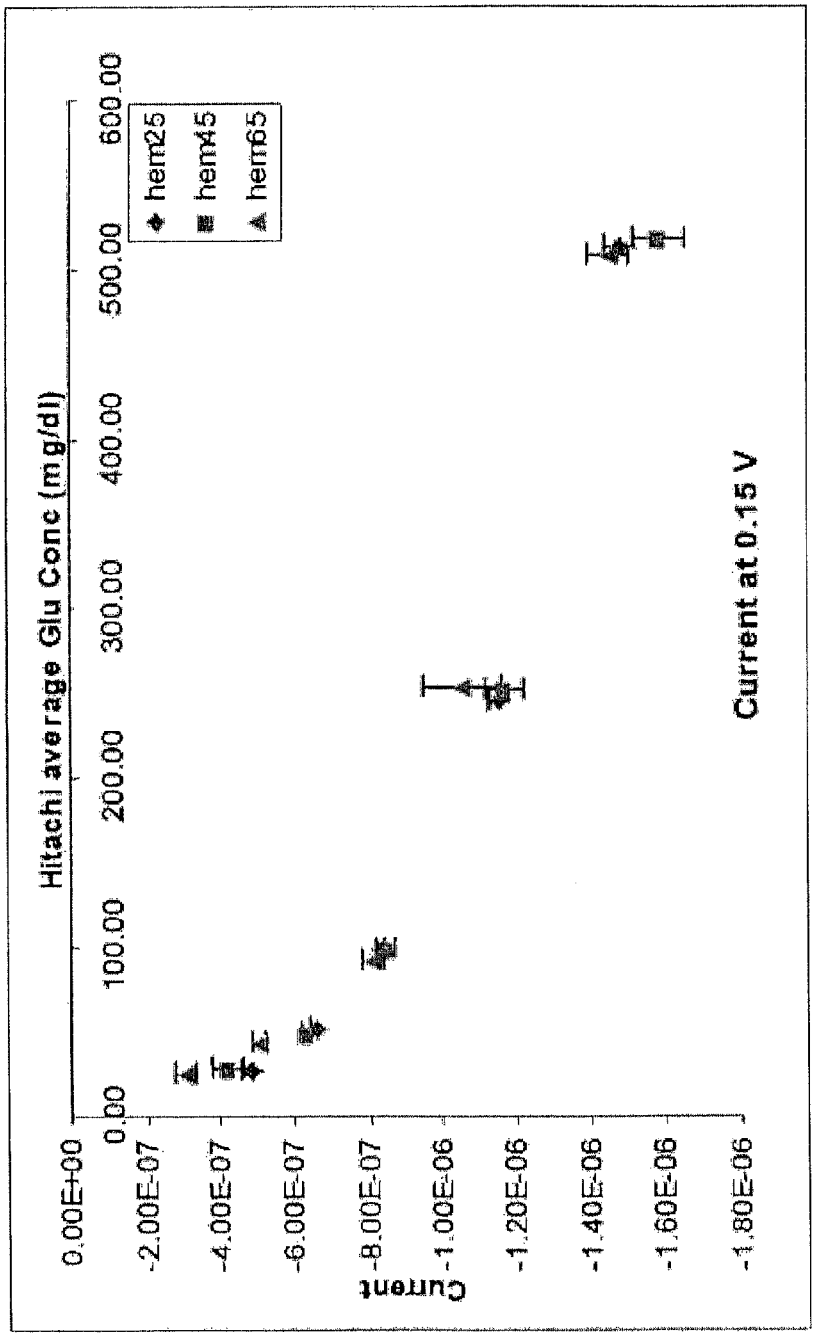
FIG. 8A is a graph illustrating current as a function of glucose concentration at 0.15 V for experiments performed in a two-electrode mode in which the pre-pulse length was doubled to 0.05 seconds.
Figure 8B:
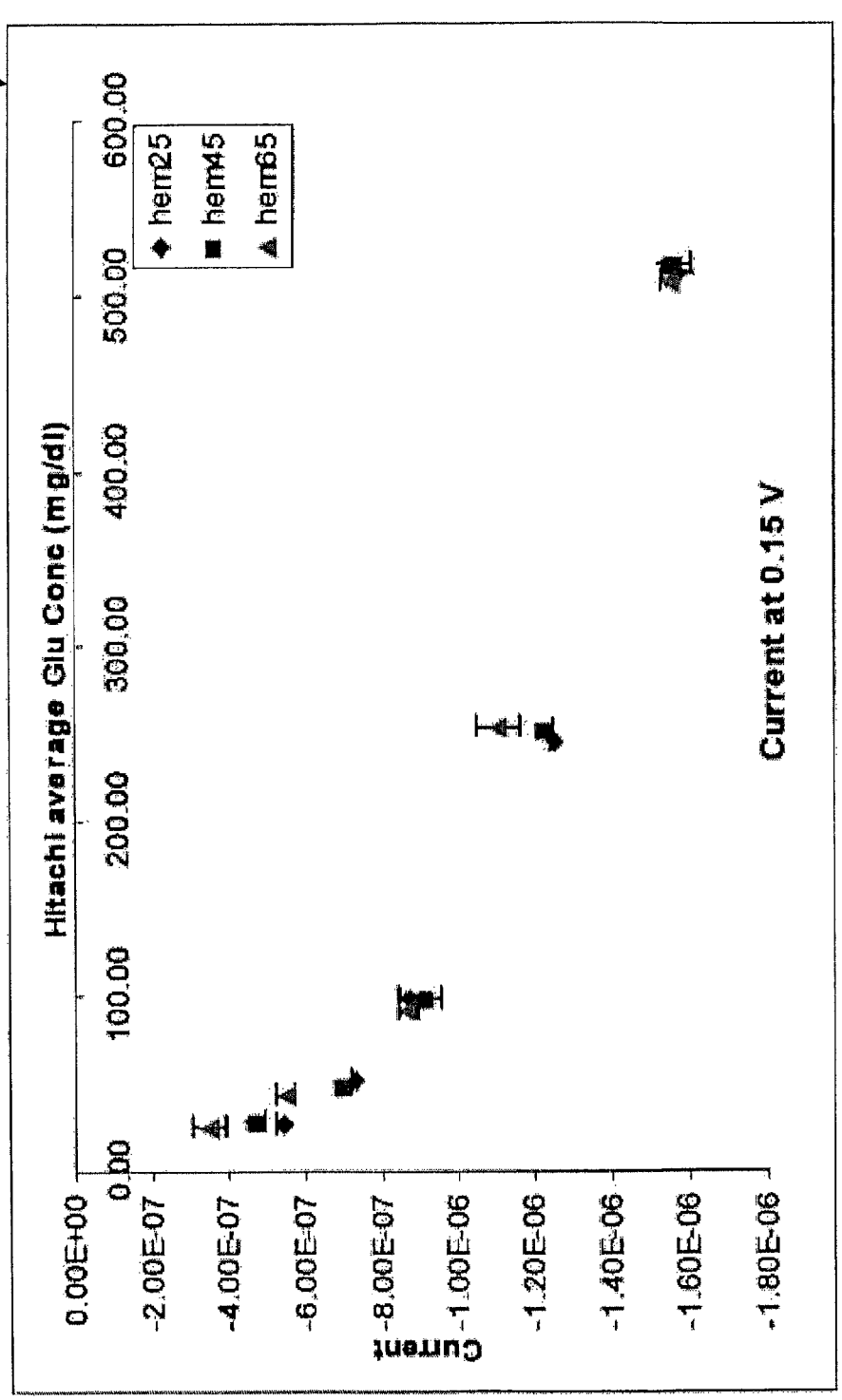
FIG. 8B is a graph illustrating current as a function of glucose concentration at 0.15 V for experiments performed in a two-electrode mode in which the pre-pulse length and the pulse length were doubled to 0.05 seconds.
Figure 8C:
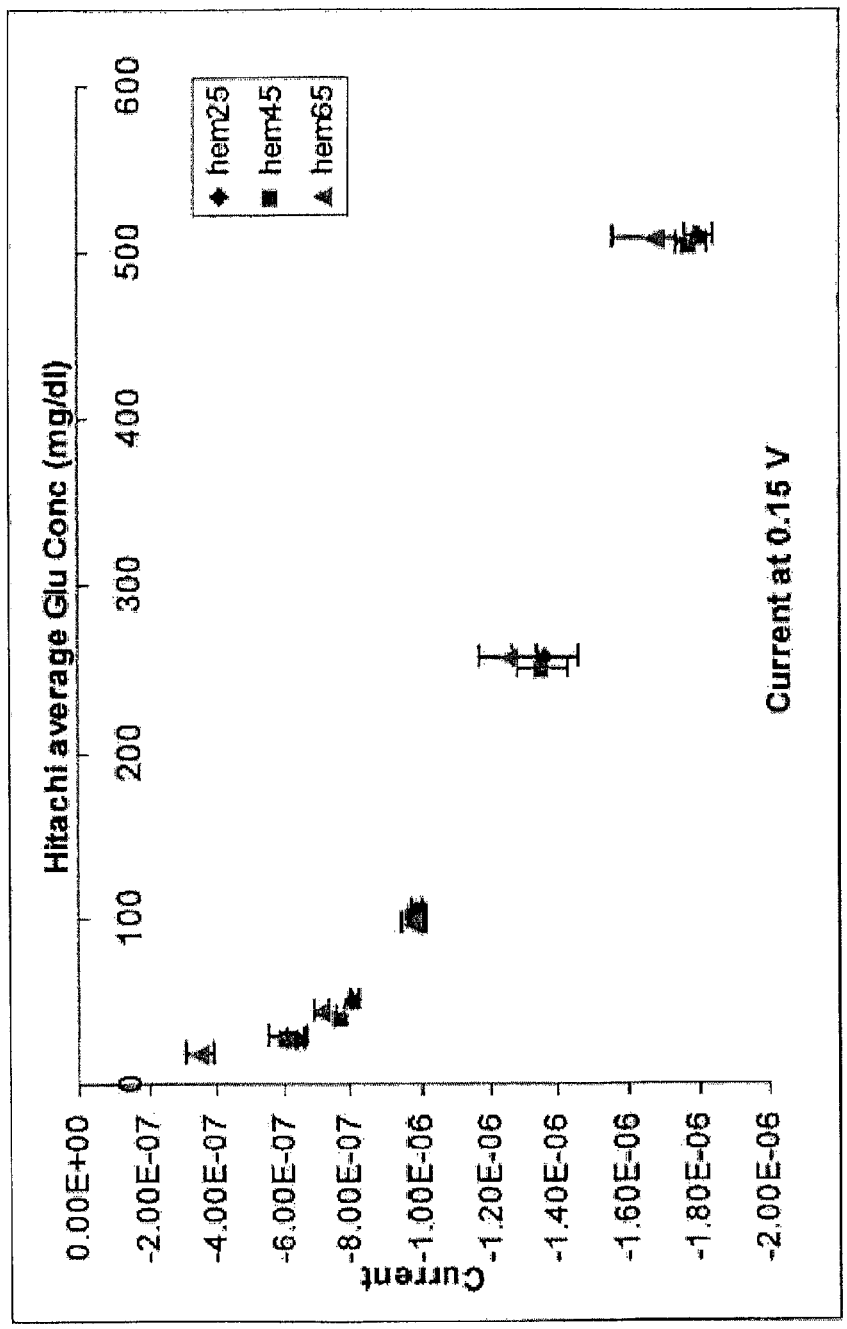
FIG. 8C is a graph illustrating current as a function of glucose concentration at a shorter potential range (0.05 to 0.25 V) for experiments performed in a two-electrode mode.

Other experimental conditions have provided comparable results to those described above. FIGS. 8A, 8B, and 8C show graphs 64, 66, 68 that illustrate current as a function of glucose concentration at 0.15 volts for experiments performed using a two-electrode type test strip 32. In the results illustrated in FIG. 8A, the pulse sequence was modified in which the pre-pulse or pulse interval length was doubled from 25 msec to 50 msec (0.05 seconds). The error bars in FIG. 8A represent a ±1 sample standard deviation unit and the current values were averaged over 10 measurements performed using the same solution. The current was measured for hematocrit levels of 25 percent, 45 percent, and 65 percent. As can be seen in FIG. 8B, the pre-pulse length and pulse length were each respectively doubled to a length of 0.5 seconds. In this particular example, the sampling rate was adjusted so that the duration of the experiment was not changed. As can be seen in the current response in FIG. 8B, the current response was similar at all hematocrit levels (25 percent, 45 percent, and 65 percent). Like before, the error bars represent a ±1 sample standard deviation unit and the current values were averaged over 10 measurements performed with the solution. FIG. 8C illustrates the current response where a shorter potential range of 0.05 to 0.25 volts was used which in turn further reduced the test time. It should be recognized from the results illustrated in FIGS. 8A, 8B, and 8C as well as the other examples that this technique is able to predict glucose and concentrations from 20 to 500 ml/dl concentration ranges with minimum hematocrit interference.

Figure 9:
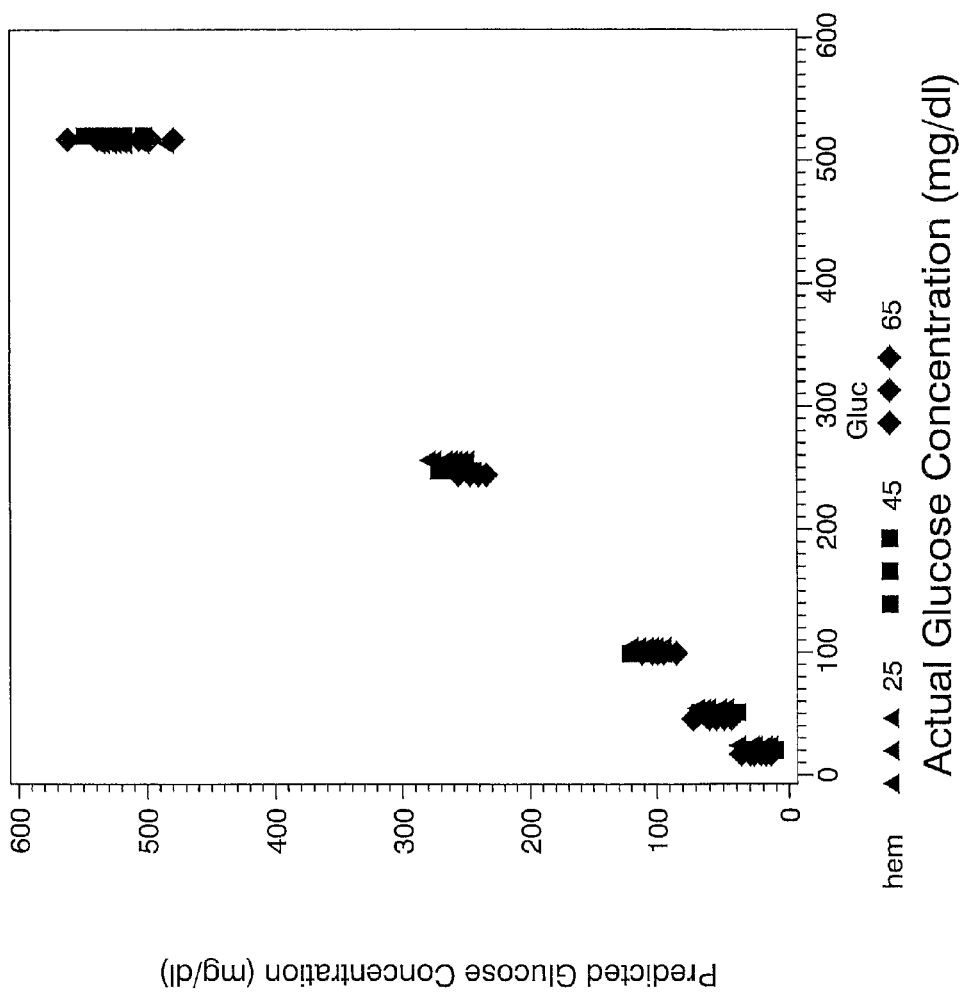
FIG. 9 is a graph comparing the predicted glucose concentration in comparison to the actual glucose concentration using 3 calibration parameters at 25, 45, and 65 percent hematocrit levels.
Figure 10:
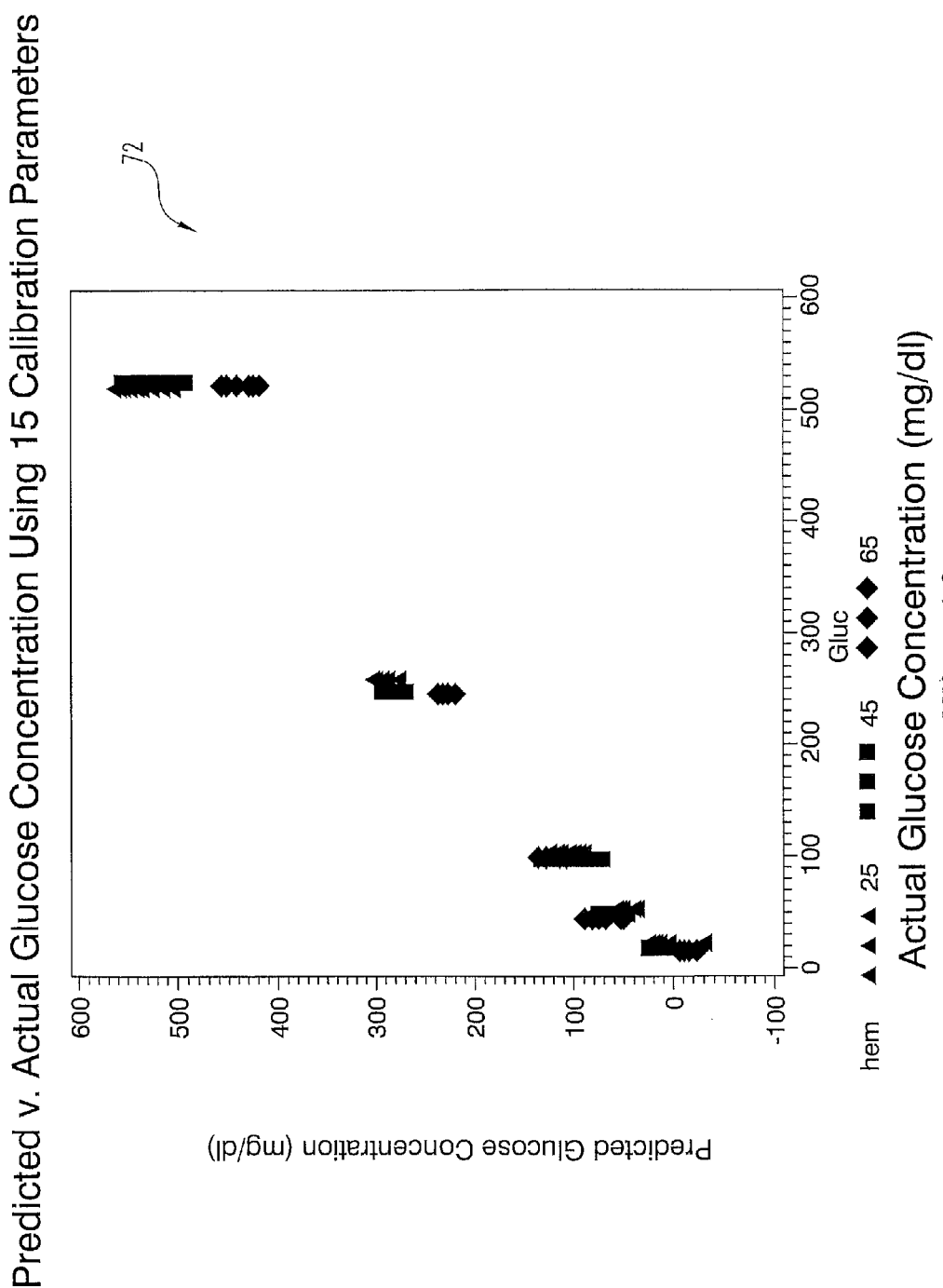
FIG. 10 is a graph comparing the predicted glucose concentration in comparison to the actual glucose concentration using 15 calibration parameters at 25, 45, and 65 percent hematocrit levels.

The accuracy of the technique can be further improved by incorporation of calibration parameters. In particular, the accuracy of the technique can be further improved by using calibration parameters instead of a single potential constant. The graph 70 in FIG. 9 illustrates the results of non-linear regression technique using three calibration parameters. In particular, the graph compares the predicted versus actual glucose concentration using 3 calibration parameters at 25 percent, 45 percent, and 65 percent hematocrit levels. The three calibration parameter example provided in FIG. 9 provides excellent correlation between the predicted and measured glucose concentration. In particular, using linear regression, the fitting coefficient ($R^2$) is 0.9692. In a similar analysis using 15 calibration parameters, which is shown in the graph 72 of FIG. 10, the fitting coefficient ($R^2$) is improved to 0.9962 for comparisons of the predicted and actual glucose concentrations used in the above-described technique at 25 percent, 45 percent, and 65 percent hematocrit levels.

A specific example of this technique for measuring glucose concentrations in blood will now be described. Initially, when the body fluid is applied to the test strip 32 for analysis, there is a 2-second quiet time to allow sufficient time for enzymatic reaction to occur. After the quiet period, the meter 34 pulses the potential to ever increasing potentials within a potential window that is below the maximum (diffusion limited) current response. In one particular form, 50 mV pulses are applied for 25 msec and are repeated every 25 msec. For every pulse, the baseline pulse is increased 4 mV. Again, the potential range or window in which the pulses are applied can vary depending on the test strip's properties, but the window is below the peak response current. The meter 34 measures the response as the difference between the current at the end of the pulse and the current just before the pulse is applied. By measuring the current just before the pulse is applied, the effect of the charging current can be reduced. The meter 34 compares the response (below the peak current) with the responses for known glucose concentrations in order to determine the measured glucose level. The meter 34 provides to the user the measured glucose level on the output device 36, such as a display.

In one example, only a few pulses are applied around 150 mV (in two-electrode mode), and the glucose concentration is determined based on the response current at one potential. However, the accuracy of the detection can be further improved by performing the measurement at three different potentials. In still yet another example, the same accuracy can be achieved when measuring over a narrow potential window but with an improvement in the measurement time. In an example for a three-electrode system, 50 mV pulses are applied in 4 mV increments to cover the −100 to 300 mV range (400 mV total).

As should be appreciated, the above-described techniques provide a diagnostic method that is simple for use in a DC type excitation signal. In addition, it allows for short sample measurement times and low potentials. In alternate embodiments, it is envisioned that when performing a single potential measurement, the detection time can be further reduced to under 5 seconds. It also should be recognized that the lower potential applied, that is below the peak, diffusion-limited current, eliminates potential contributions from common sources of interference.

It should be recognized that a potentiostat and a meter be interchangeably used to perform the techniques described herein. Although a number of the above-discussed test results were generated using a potentiostat, it should be recognized that a meter can be used instead, especially in home diagnostic settings. The meter 34 can include components, such as a display, speaker, processor, memory, a power source such as a battery, and/or electrical contact leads for connecting to the test strip 32. However, it should be appreciated that other types of electronic devices, besides the illustrated meter, can utilize these measurement techniques. In one particular example, an Aviva® brand test strip sold by Roche Diagnostics is used, but it should be recognized that the above-described techniques can be adapted for use in other types of test strips 32. For example, the techniques can be used to analyze glucose concentrations using two-electrode or three-electrode (or more) electrochemical type test strips. Depending on the electrode arrangement, the potential windows may vary. In one particular form, an Aviva® brand test strip is used with the technique. This technique provides an alternative measurement method for determining blood glucose concentrations in contrast to the current technique used for Aviva® type systems. By using only DC excitation at low potentials, the electronics and other systems in the meter can be simplified, and short measurement times can be achieved. For example, the test can be completed within 5 seconds of drop detection. Moreover, the low applied potential can eliminate the contribution of common interferants to the current response, thereby providing more accurate results.

As used in the specification and claims, the following definitions apply:

The term "differential pulse voltammetry" is used in a broad sense and is meant to include an electrical measurement technique in which a series of regular voltage pulses are superimposed on a potential linear or stair step sweep. The current is measured immediately before and after each potential change and the current differential is plotted as a function of potential. The wave form of the pulse can be a square shape or may include other shape-type pulses.

The term "diffusion layer" includes a region usually in the vicinity of the working electrode in which concentration of the analyte being measured differs from the bulk concentration of the solution. This expansion of the diffusion layer results in a fall off of the current proportional to $T^{1/2}$. Diffusion is the movement of material from a high concentration region to a lower concentration region. The peaking current is observed due to the combined effect of the decrease of electro surface concentration and the expansion of the diffusion layer with time.

The language used in the claims and specification is to only have its plain and ordinary meaning, except as explicitly defined above. The words in the above definitions are to only have their plain and ordinary meaning Such plain and ordinary meaning is inclusive of all consistent dictionary definitions from the most recently published Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A method, comprising:
analyzing glucose concentration in a body fluid received in a biosensor through differential pulse voltammetry, wherein the biosensor at least includes a reagent covering a working electrode, said analyzing including
applying short, high frequency voltage pulses to the body fluid in the biosensor to keep a diffusion layer within the reagent of the working electrode, wherein the voltage of the pulses are incrementally increased,
determining the glucose concentration of the body fluid based only on a response to the pulses within a voltage window that is less than a voltage where a peak, diffusion-limited current occurs, and
outputting glucose concentration results from said determining.

2. The method of claim 1, wherein the voltage window is from −0.05 V to 0 V.

3. The method of claim 1, wherein the voltage window is no more than 300 mV.

4. The method of claim 1, wherein said determining includes performing a single measurement.

5. The method of claim 1, wherein the voltage window is 0.05 V to 0.25 V.

6. The method of claim 1, wherein during said applying the pulses have a pulse length of 25 msec, a pulse interval 25 msec, a pulse voltage 50 mV, and a voltage step 4 mV.

7. The method of claim 1, wherein during said applying the pulses have a pulse interval of 50 msec.

8. The method of claim 7, wherein during said applying the pulses have a pulse length of 50 msec.

9. The method of claim 1, further comprising:
wherein a meter performs said outputting the glucose concentration results;
detecting dosing of the body fluid into the biosensor with the meter before said applying; and
where no more than 5 seconds elapse between said detecting dosing of the body fluid and said outputting the glucose concentration results.

10. The method of claim 1, further comprising:
detecting dosing of the body fluid into the biosensor before said applying; and
allowing the body fluid to incubate for 2 seconds before said applying.

11. The method of claim 1, wherein no incubation period occurs.

12. The method of claim 1, wherein said determining includes measuring difference between current at the end of each pulse and current just before each pulse.

13. The method of claim 1, wherein said determining includes adjusting the response based on or more calibration parameters.

14. The method of claim 1, wherein the biosensor has a two-electrode configuration.

15. The method of claim 1, wherein the biosensor has a three-electrode configuration.

16. A method, comprising:
analyzing glucose concentration in a body fluid with differential pulse voltammetry, wherein said analyzing includes
applying one or more pulses to the body fluid in a voltage window that is less than a voltage where a peak, diffusion-limited current occurs, and
determining the glucose concentration based only on a response to the pulses in the voltage window.

17. The method of claim 16, wherein the voltage window is from −0.05 V to 0 V.

18. The method of claim 16, wherein the voltage window is no more than 300 mV.

19. The method of claim 16, wherein said determining includes performing a single measurement.

20. The method of claim 16, wherein the voltage window is 0.05 V to 0.25 V.

21. The method of claim 16, wherein during said applying the pulses have a pulse length of 25 msec, a pulse interval 25 msec, a pulse voltage 50 mV, and a voltage step 4 mV.

22. The method of claim 16, wherein during said applying the pulses have a pulse interval of 50 msec.

23. The method of claim 22, wherein during said applying the pulses have a pulse length of 50 msec.

24. The method of claim 16, further comprising:
detecting dosing of the body fluid into a biosensor before said applying;
outputting with a meter glucose concentration results from said determining; and
where no more than 5 seconds elapse between said detecting dosing of the body fluid and said outputting the glucose concentration results.

25. The method of claim 1, wherein said determining includes adjusting the response based on or more calibration parameters.

* * * * *

UNITED STATES PATENT AND TRADEMARK OFFICE
CERTIFICATE OF CORRECTION

PATENT NO. : 8,691,075 B2
APPLICATION NO. : 12/649929
DATED : April 8, 2014
INVENTOR(S) : Georgeta C. Lica Page 1 of 1

It is certified that error appears in the above-identified patent and that said Letters Patent is hereby corrected as shown below:

In the Claims
Col. 10, Claim 25, line 46, replace "on or more" with --on one or more--

Signed and Sealed this
Twenty-second Day of July, 2014

Michelle K. Lee
*Deputy Director of the United States Patent and Trademark Office*